(12) United States Patent
Tozzi et al.

(10) Patent No.: US 9,901,433 B2
(45) Date of Patent: Feb. 27, 2018

(54) MEDICAL DEVICE COMPRISING AN ARTIFICIAL CONTRACTILE STRUCTURE

(71) Applicant: MYOPOWERS MEDICAL TECHNOLOGIES SA, Lausanne (CH)

(72) Inventors: Piergiorgio Tozzi, Lausanne (CH); Daniel Hayoz, Villars sur Glane (CH); Martin Horst, Horw (CH); Marco Wieland, Bale (CH); Merg Burkhard, Bickenbach (DE); Peter Zeyher, Darmstadt (DE)

(73) Assignee: MYOPOWERS MEDICAL TECHNOLOGIES FRANCE, Saint-Louis (FR)

(*) Notice: Subject to any disclaimer, the term of this patent is extended or adjusted under 35 U.S.C. 154(b) by 0 days.

(21) Appl. No.: 15/356,686

(22) Filed: Nov. 21, 2016

(65) Prior Publication Data

US 2017/0065402 A1 Mar. 9, 2017

Related U.S. Application Data

(63) Continuation-in-part of application No. 13/519,179, filed as application No. PCT/EP2011/003286 on Jul. 1, 2011, now abandoned.

(30) Foreign Application Priority Data

Jul. 2, 2010 (EP) ..................................... 10168228

(51) Int. Cl.
*A61F 2/08* (2006.01)
*A61F 2/00* (2006.01)
(Continued)

(52) U.S. Cl.
CPC ......... *A61F 2/0036* (2013.01); *A61M 1/1068* (2013.01); *A61M 1/122* (2014.02); *A61F 2/2481* (2013.01); *A61F 2002/482* (2013.01)

(58) Field of Classification Search
USPC ....... 623/14.13, 24–26; 600/29–31; 604/8–9; 606/201–202; 417/410.1–417
See application file for complete search history.

(56) References Cited

U.S. PATENT DOCUMENTS 6,162,238 A 12/2000 Kaplan et al.
2006/0047180 A1 3/2006 Hegde et al.
(Continued)

FOREIGN PATENT DOCUMENTS

EP 1238638 5/2004
EP 1598030 6/2008
(Continued)

OTHER PUBLICATIONS

International Search Report dated Feb. 17, 2012, in corresponding PCT application.
(Continued)

*Primary Examiner* — Yashita Sharma
(74) *Attorney, Agent, or Firm* — Young & Thompson

(57) ABSTRACT

A medical device including an artificial contractile structure, which may be advantageously used to assist the functioning of a hollow organ, is provided. The medical device includes an artificial contractile structure including at least one contractile element adapted to contract an organ in such a way that the contractile element is in a resting or in an activated position; at least one actuator designed to activate the contractile structure; and at least one source of energy for powering the actuator. The actuator includes an electromotor and a transmission element linking the electromotor to the contractile element, the transmission element being configured to transmit to the contractile element a force induced by the electromotor. The electromotor includes an electric motor, a gear head connected to the motor, a lead screw cooperating with a nut mounted on the lead screw, the lead screw or the nut being connected to the transmission element and cooperating with the gear head to transmit the force induced by the electromotor on the transmission element. The ratio "current which is needed to maintain the contractile element in its activated position/current which is needed
(Continued)

to change the position of the contractile element" is less than 1/500.

25 Claims, 5 Drawing Sheets

(51) Int. Cl.
*A61M 1/10* (2006.01)
*A61M 1/12* (2006.01)
A61F 2/48 (2006.01)
A61F 2/24 (2006.01)

(56) References Cited

U.S. PATENT DOCUMENTS

2009/0259093 A1 10/2009 Bhat et al.
2010/0145138 A1 6/2010 Forsell

FOREIGN PATENT DOCUMENTS

| JP | 07-051304 | 3/2007 |
| WO | 2004066879 | 8/2004 |
| WO | 2007066344 | 6/2007 |
| WO | 2009004092 | 1/2009 |
| WO | 2009048379 | 4/2009 |
| WO | 2009048399 | 4/2009 |

OTHER PUBLICATIONS

European Search Report dated Nov. 11, 2010, in corresponding application EP 10 16 8228.
Richter et al., "Retropubic versus Transobturator Midurethral Slings for Stress Incontinence", The New England Journal of Medicine, 2010; 362:2066-2076.

MEDICAL DEVICE COMPRISING AN ARTIFICIAL CONTRACTILE STRUCTURE

TECHNICAL FIELD

The present invention relates to a medical device comprising an artificial contractile structure activated by an actuator, which may be advantageously used to assist the functioning of an organ, e.g. a sphincter or the heart. More generally, it can be used for moving or constricting a hollow or a tubular part of the body in such a way as to reduce its diameter.

BACKGROUND OF THE INVENTION

It is known to use artificial structures to assist muscular contraction. Such structures are adapted to assist atrial or ventricular contraction, or to assist or replace a natural sphincter. The use of such artificial sphincters has increased in recent years because faecal and urinary incontinences now affects more than 10% of people over 60 years of age and dramatically increases in patients over 80 years of age. Several pharmaceutical or surgical solutions have been developed for treating urinary and faecal incontinences. Generally, the outcome of surgery for treatment of urinary and faecal incontinence has to be regarded as low. The impacts on health care costs and overall quality of life of the patient are enormous.

The AMS800 artificial sphincter for urinary incontinence is commercialized by American Medical Systems and is composed of three components, a cuff, a pump, and a pressure-regulating balloon. The cuff is implanted at the bulbous urethra in males and is inflatable by means of a fluid. The pump is implanted in the scrotum and the pressure-regulating balloon is implanted in the abdomen. The major problems when using AMS800 is the tissue erosion around the urethra due to the constant pressure, the atrophy and irritation of tissues at the location of the inflatable cuff, and the emergency surgery for repair should the device remain in closed position in the event of mechanical failure. All other commercialized artificial sphincters whether for urinary or faecal incontinences bear similar drawbacks.

The ProAct™ artificial sphincter for urinary incontinence is commercialized by Uromedica and is composed of two small implantable balloons. During a short outpatient procedure, the balloons are surgically placed under the skin in the area where the prostate of the patient was surgically treated. The balloons help protect against accidental leaking of urine by increasing the amount of pressure required to urinate. When the patient needs to urinate, a normal amount of effort still should be required to push the urine out. However, the pressure from the balloons will help guard against unintentional urine loss, such as during a sneeze or cough. The major problems when using ProACT™ are identical to the problems using AMS800 artificial sphincter described above.

FlowSecure™, manufactured by Sterilin Ltd, another silicone hydraulic urinary sphincter similar to AMS800, has an extra pressure transmission balloon to transfer increased intra abdominal pressure directly to the cuff. Implantation of this device is technically feasible, but still difficult and is reported to be safe and effective in the short-term for the treatment of male urodynamic stress urinary incontinence, arising from a number of etiologies. However, the major problems when using FlowSecure™ are identical to the problems using AMS800 artificial sphincter described above.

Some publications describe the use of artificial sphincters comprising shape memory alloy elements suitable for opening and closing a part of an organ in a living body. EP 1 238 638 describes an artificial sphincter having an opening/closing portion for opening and closing, wherein said opening/closing portion has:
 a pair of elongated shape memory alloy elements that change reversibly between opposite shapes upon changes in temperature, and
 hinges that link said pair of shape memory alloy elements together in a cylindrical shape.

Such artificial sphincter is placed around the intestine of a human or animal inside the body near to an intestinal opening so that the opening/closing portion constricts the intestine. When the shape memory alloy elements are heated, they change shape, so that the constricting force on the intestine is lost.

However, as the opening/closing portion is still constricting the same region of the intestine, there is likely damage to this part of the body, and more especially a risk of tissue erosion, atrophy and burns, due to the constant pressure and heating of the shape memory alloy elements.

Reversible thermal lesions occur when the local temperature is increased to the 42° C. to 44° C. range (5 C-7° C. over the normal body temperature of 37° C.) and that irreversible thermal lesions occur when the local temperature is increased above 45° C. (>8° C. temperature rise over 37° C., which is the normal temperature). The time over overheating also plays an important role.

Moreover, in normal state, the shape memory alloy elements are not heated and are each bent to constrict the intestine. That means that heating is necessary to open the artificial sphincter. If the heating means fail, the sphincter remains closed and cannot be opened what may be leading to life threatening complications. An emergency surgery is then necessary to open the artificial sphincter to solve the problem.

Another artificial sphincter has been proposed in JP 07-051304. This document describes a constrictor comprising two shape memory alloy elements with different shape memories, and covered by covering materials. The first covering material is formed in a shape to close the urethra in the daytime, and the second covering material is formed in a shape to half close the urethra in the night. This sphincter allows changing the pressure to the urethra, in order to prevent the incontinence in life action in the daytime, and to avoid necrosis of the tissue by loosing the pressure to the urethra in the night.

However, the drawbacks of such artificial sphincters are that there is a risk of tissue erosion and consequential necrosis, due to the high constant pressure to the urethra during the day and that there is a risk of incontinence during the night. If the shape memory alloy is no more efficient or is broken, the whole sphincter should be moved and replaced.

Moreover, JP 07-051304 discloses an artificial sphincter in which the shape memory alloy elements are disconnected from each other. This embodiment does not allow optimal pressure control.

Moreover, this kind of shape memory alloy elements uses a lot of power. That means that the battery needs to be changed very often or alternatively very large batteries have to be used.

EP 1 598 030 discloses a urine incontinence treatment apparatus, comprising a restriction device for engaging the urethra to form a restricted urine passageway in the urethra, the restriction device being operable to change the restriction of the urine passageway, a source of energy, and a control device operable from outside the patient's body for controlling the source of energy to release energy for use in connection with the operation of the restriction device, a motor or pump implantable in the patient, wherein the source of energy is adapted to power the motor or pump and the control device is adapted to control the motor or pump to operate the restriction device. The source of energy can be an internal battery with a lifetime of at least 10 years. However, as disclosed in EP 1 598 030, an internal battery is an advantageous solution for embodiments of the apparatus that have a relatively high consumption of energy, which cannot be satisfied by direct supply of wireless energy. Therefore, even if the lifetime of the internal battery is of 10 years, the operation time of said internal battery is shorter as the energy consumption is very high. Said internal battery should therefore be changed very often.

WO 2009/048399 discloses an apparatus for controlling a flow of sperms in an uterine tube, comprising an implantable flow influence device to be applied on at least one portion of the uterine tube. The energy source is a implantable primary battery or accumulator. Preferably the energy source is external and a control device controls the external energy source to transmit wireless energy from the outside of the patient's body to the inside. The energy will directly be used or the operation of the device e.g. to power the constriction/stimulation unit. The internal source may store energy. The constriction/stimulation device needs high energy to be activated but also to be maintained in an activated position. Therefore the preferable energy supply is the wireless transmission of energy. A drawback of wireless transmission is its efficiency. In case of using an accumulator for storing energy the accumulator has to be recharged frequently that reduces the lifetime of the accumulator.

WO 2009/004092 discloses an artificial structure comprising several contractile elements adapted to contract an organ by means of contractile fibers. Such fibers need high energy to be activated but also to be maintained in an activated position. As disclosed in WO 2009/004092 an implanted rechargeable battery needs to be recharged at least once a day using a battery volume in the range of this invention. Larger rechargeable batteries with more capacity exist but would not be possible to implant.

WO 2004/066879 discloses a male sexual impotence treatment apparatus, comprising a constriction member extending in a loop around the penile tissue. Wireless energy transfer is used to electrically power the constriction member during device operation that means external energy is wireless transmitted from the outside of the patient's body to the inside to recharge the implantable battery. The energy will directly be used or the operation of the device or to recharge the battery. The actuator is fixed on the constriction member in such a way that an electric wire linking the actuator to a source of energy goes through the body of the patient. A drawback of wireless transmission is its efficiency. Another drawback is the recharging of the battery. Small rechargeable batteries have to be replaced after about 1 year.

WO 2007/066344 discloses an implantable extra cardiac compression device for left ventricular assistance in severe heart failure. The device comprises metal flanges that are passively flexed at springed-hinges by a vertically moving metal cup. The flanges are connected to each other by a high-tensile, elastic polymer membrane. However, with such device, one flange, used alone, cannot contract the organ. Moreover, such device needs high energy to be activated but also to be maintained in an activated position. The external battery that may be recharged will be connected transcutaneously to the motor assembly placed inside the patient's abdomen. A transcutaneous connection always bears a risk of infection.

Therefore there are, at the present time, no adequate solutions, whether commercial or in the literature, for implanting battery-powered devices aimed at frequently pressing organs, whereby the battery can operate for a couple of years without recharging.

SUMMARY OF THE INVENTION

The present invention provides a medical device comprising an artificial contractile structure, which allows one to avoid the disadvantages of the prior art.

Accordingly, the present invention relates to a medical device comprising:
an artificial contractile structure comprising at least one contractile element adapted to contract an organ, said contractile element being in a resting position or in an activated position, the activated position being defined by said contractile element constricting the organ and the resting position being defined by said contractile element not constricting the organ,
at least one actuator designed to activate said contractile structure, and
at least one source of energy for powering said actuator,
wherein the actuator comprises an electromotor and a transmission element linking the electromotor to the contractile element, the transmission element comprising a cable and being configured to transmit to the contractile element a force induced by the electromotor, and
wherein said electromotor comprises an electric motor, a gear head connected to said motor, a lead screw cooperating with a nut mounted on said lead screw, said lead screw or said nut being connected to said transmission element and cooperating with said gear head to exert a force on said transmission element, and
wherein the ratio of current needed to maintain the contractile element in the activated position/current needed to change the position of the contractile element is less than 1/500.

According to the invention, the ratio "current which is needed to maintain the contractile element in its activated position/current which is needed to change the position of the contractile element" is less than 1/500, preferably less than 1/800, and more preferably less than 1/1000.

Advantageously, the ratio "current which is needed to maintain the contractile element in its activated position/current which is needed to change the position of the contractile element" is comprised between 1/20000 and 1/500, preferably between 1/14000 and 1/800, and more preferably between 1/8000 and 1/1000.

Advantageously, the energy consumption of said medical device is less than 2000 mAh/year, preferably less than 1800 mAh/year for a continuous pressure applied on the organ which is less than 5 N/cm$^2$. Preferably, this pressure is applied alternatively through independent contractile elements.

Preferably, the energy consumption of the medical device is less than 1800 mAh/year, and preferably less than 1500 mAh/year for a continuous pressure applied on the organ, which is less than 2.5 N/cm$^2$. Preferably, this pressure is applied alternatively through independent contractile elements.

Preferably, the source of energy has a volume less than 20 cm$^3$.

Advantageously, the source of energy may be selected to have an operation time comprised between 2 months and 10 years, preferably between 1 year and 10 years, and more preferably between 2 years and 8 years, optimally 5 years.

Preferably, the actuator may comprise at least one electromotor and transmission means linked to the contractile element and designed to transmit to the contractile element a force induced by the electromotor.

In some preferred embodiments, the artificial contractile structure may comprise at least two contractile elements being distributed along a support in order to be able to reduce the volume of the organ to be contracted in at least two distinct regions of the organ. Preferably, the medical device may further comprise at least two actuators respectively linked to their corresponding contractile element by their corresponding transmitting means. Each contractile element is able to contract a portion of the organ and to be activated or in a resting position independently of the position of the other contractile elements.

The medical device may further comprise a control unit which is adapted to activate each contractile element pulsatory and alternately independently from each other.

In a preferred embodiment, the actuator may be designed so that the contractile element applies, in a pulsating and alternating manner, a pressure on an organ to be contracted during a period comprised between 30 seconds to 90 minutes, preferably between 30 seconds to 60 minutes, more preferably between 30 seconds to 45 minutes, and more preferably between 10 minutes and 30 minutes. Preferably, the strength is such that the different regions of the organ are completely closed in a pulsating and alternating manner.

The present invention relates also to a medical device comprising:
- an artificial contractile structure comprising at least two contractile elements adapted to contract an organ, in such way that said contractile element are able to be in a resting or in an activated position, the activated position being defined with said contractile element constricting the organ and the resting position being defined with said contractile element not constricting the organ,
- wherein said contractile elements are able to be maintained in the same position at the same time.

More particularly, said contractile elements may be able to be maintained in their activated position at the same time, preferably for sport activities of a patient. Said contractile elements may also be able to be maintained in their resting position at the same time, preferably for sleep activities of a patient. Said contractile elements may further be able to be actuated pulsatory and alternately independently from each other.

The present invention relates also to a medical device comprising:
- an artificial contractile structure comprising at least one contractile element adapted to contract an organ, in such way that said contractile element is in a resting or in an activated position, the activated position being defined with said contractile element constricting the organ and the resting position being defined with said contractile element not constricting the organ,
- at least one actuator designed to activate said contractile structure,
- at least one source of energy for powering said actuator,
- wherein it further comprises safety means designed to change automatically the position of the contractile element.

This feature of this medical device may be used separately or in combination with anyone of the features of the medical device described above.

Advantageously, said safety means are designed to move automatically the contractile element from its activated position into its resting position. More particularly, said safety means are designed to move automatically the contractile element from its activated position into its resting position if the pressure applied on the organ is higher than a preset pressure or if the power of the source of energy is less than a preset power.

Advantageously, said safety means are designed to move automatically the contractile element from its resting position into its activated position for example if the time for which the organ is not constricted is higher than a preset time.

Advantageously, the present invention provides a medical device comprising an artificial contractile structure, which is designed for chronic applications (i.e. long-term implantation), for example for many months and preferably many years.

Such devices may be used in several indications, e.g. for assisting or replacing a natural sphincter, especially for the treatment of faecal or urinary incontinence, for assisting atrial or ventricular contraction, for assisting the respiratory function, for assisting or replacing a paralyzed muscle or for treating venous insufficiency. The present invention is particularly designed for improving sphincter muscle function and therefore to improve the patient's quality of life with a significant reduction of treatment costs.

DETAILED DESCRIPTION OF THE INVENTION

Figure 1:
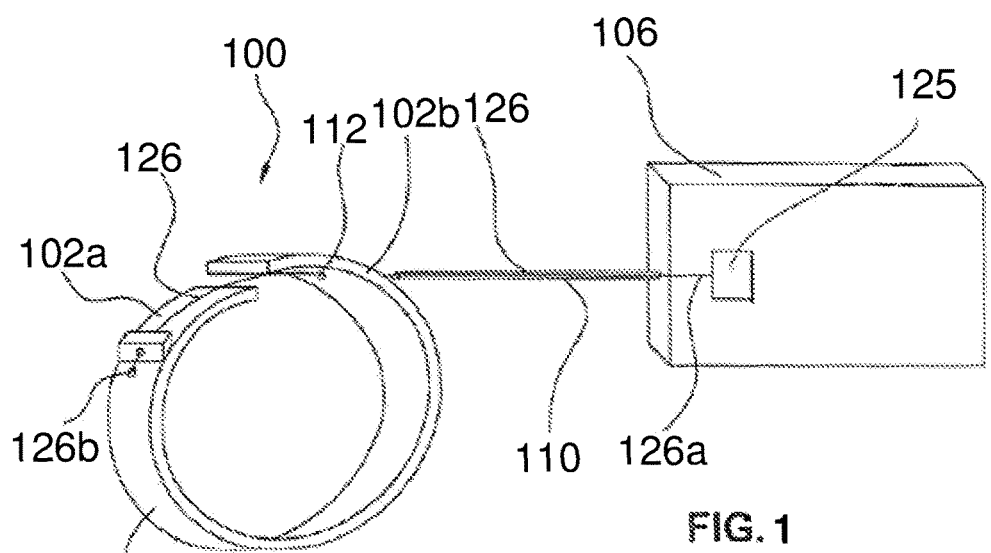
FIG. 1 is a schematic view of a medical device according to the present invention, the contractile element being in resting position.

In the present description, the term "organ" covers any organ of the human body, preferably an organ comprising a hollow part, containing fluids as for example the ventricular part of the heart, or a region of an organ in the living body having an overall cylindrical shape, for example a blood vessel, the urinary tract, the colon, the stomach or any other body part against which pressure can be applied.

In the present description, the term "electromotor" covers any device designed to produce motion and mechanical effects by the action of electricity.

In the present description, the term "constrict" means that the contractile element applies a pressure against a region of an organ around or on which said contractile element has been placed.

In the present description, the term "pulsatory" means that each contractile element is activated and deactivated in alternation with another contractile element to constrict or apply a pressure or not against the region of the organ or the hollow part around or on which it has been placed, preferably so as to close or open said region of the organ or of the hollow part. More especially, in a preferred embodiment, contractile element one is closed for a certain time, while the other contractile element(s) are open. After a given time the contractile element two will be closed while the contractile element one is still closed. When contractile element two is closed, contractile element one opens, and so on. The frequency of alternate activation is dependent upon the nature of the tissues and inside organ pressure, and is adjusted so that no tissue erosion and burn appear after several months of implantation.

In the present description, the term "continuous" means that a pressure is applied against at least one region of the organ in such a way that said organ is closed during all the time for which the medical device is used, except the short periods for which the organ should be open.

In the present description, the term "link" means a direct or indirect connection between two elements.

The medical device comprises:
- an artificial contractile structure comprising at least one contractile element adapted to contract an organ, in such way that said contractile element is in a resting or in an activated position, the activated position being defined with said contractile element constricting the organ and the resting position being defined with said contractile element not constricting the organ,
- at least one actuator designed to activate said contractile structure and separated from the contractile structure,
- at least one source of energy for powering said actuator,
- at least one control unit for controlling the actuator.

According to the invention, said source of energy has a volume less than 20 $cm^3$, preferably less than 15 $cm^3$ and most preferably less than 12 $cm^3$.

Moreover, the ratio "current which is needed to maintain the contractile element in its activated position/current which is needed to change the position of the contractile element" is less than 1/500, preferably less than 1/800, and more preferably less than 1/1000. Preferably, the ratio "current which is needed to maintain the contractile element in its activated position/current which is needed to change the position of the contractile element" is comprised between 1/20000 and 1/500, preferably between 1/14000 and 1/800, and more preferably between 1/8000 and 1/1000.

Advantageously, the actuator comprises actuating means designed in such a way that the energy consumption of said medical device which is needed to change the position of the contractile element is less than 2000 mAh/year and preferably less than 1800 mAh/year and in such a way that the energy consumption of said medical device which is needed to maintain the contractile element in its activated position is less than 200 mAh/year for a continuous pressure applied on the organ by the contractile element, which is in its activated position, comprised between 0.1 $N/cm^2$ and 5 $N/cm^2$. Preferably, this pressure is applied alternatively through independent contractile elements.

Preferably, said actuating means are designed in such a way that the energy consumption of the medical device which is needed to change the position of the contractile element is less than 1350 mAh/year and in such a way that the energy consumption of said medical device which is needed to maintain the contractile element in its activated position is less than 150 mAh/year for a continuous pressure applied on the organ by the contractile element, which is in its activated position, comprised between 0.3 $N/cm^2$ and 2.5 $N/cm^2$. Preferably, this pressure is applied alternatively through independent contractile elements.

Advantageously, the current consumption of the medical device of the invention which is needed to change the position of the contractile element for five years is comprised between 350 mAh and 9000 mAh, preferably between 350 mAh and 6750 mAh, and the current consumption of said medical device which is needed to maintain the contractile element in its activated position is comprised between 150 mAh and 1000 mAh for a continuous pressure applied on the organ by the contractile element, which is in its activated position, comprised between 0.1 $N/cm^2$ and 5 $N/cm^2$, preferably between 0.3 $N/cm^2$ and 2.5 $N/cm^2$, Preferably, this pressure is applied alternatively through independent contractile elements.

Advantageously, the actuator is separated from the contractile structure. That means that the actuator is not fastened on the contractile structure or on the contractile element. Preferably, the actuator is removably connected to the contractile structure in order to allow safe and easy maintenance and replacement of the actuator and/or the contractile structure throughout life of a patient.

Said actuator comprises at least one electromotor linked to the transmission means, which are designed to transmit to the contractile elements a force induced by said electromotor.

In a first embodiment, said electromotor may comprise an electric motor, a gearhead connected to said motor, a lead screw cooperating with said gearhead, and a nut mounted on said lead screw and linked to said transmissions means.

Figure 6:
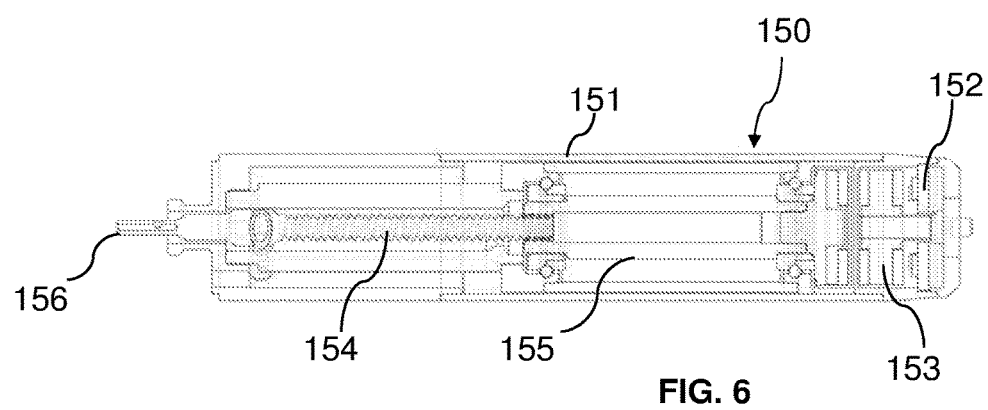
FIG. 6 represents a longitudinal cross-section of an actuator for the medical device of the invention in a preferred embodiment.

In a second embodiment represented in FIG. 6, said electromotor may comprise an electric motor, a gearhead connected to said motor, a lead screw cooperating with said gearhead, and a lead screw connected at an end with them said transmissions means and longitudinally displaceable in the actuator in cooperation with a nut hold in said actuator about the lead screw.

The actuator may further comprise sensors designed to indicate the position of the nut or the force applied by the actuator.

The transmission means may be mechanical, hydraulic, electromechanical or pneumatic. Preferably, the transmission means may be a cable linking the nut to the contractile element. The cable may be protected by a coaxial sheath. The sheath can be made for example of silicone, polyimide, PTFE composites (PTFE and fluoroethylkene polymers), pure PTFE, or other appropriate polymers. The sheath can be additionally coated with silicone, if necessary. Cables are well known in surgery. The cables can be made for example out of polyamide like Nylon®, polyether block amide, PTFE, or other appropriate polymers. Alternatively, other materials, as stainless steel or titanium, can be used. Surgeon is used to place cables in the human body. One end of the cable may be connected liquid tight to the contractile element and the other end of the cable is linked liquid tight to the nut or the lead screw of the actuator. In the present description, the terms "liquid tight" means liquid tight also humidity tight or hermetic sealed. Moreover, in some embodiments, one end of the cable may be reversibly connected to the contractile element and the other end of the cable may be reversibly linked to the nut or the lead screw of the actuator in such a way that the cable may be separated from the contractile element or from the actuator.

The source of energy can be implantable or placed outside the body of the patient.

In a preferred embodiment, the actuator and its control unit, and the source of energy are implantable and are placed in the same closed box, separated from the contractile structure or from the contractile elements. In other embodiments, the control unit and the source of energy can be also separated in two boxes (control unit and power supply unit) and connected with an electric cable, which should be easily detachable. In other embodiments, the actuator and its control unit is implantable and the source of energy is placed outside the body of the patient. In some embodiments, the source of energy comprises at least one implantable rechargeable battery with an implantable antenna and an external battery. Such implantable battery is for example a Lithium-ion or Lithium Polymer rechargeable battery commercialized by GreatBatch and others. The energy transfer system that is needed to recharge the battery is preferably through wireless connection. Such system can comprise a recharge unit, as a belt, comprising an external battery. The patient should wear the recharge unit for a number of hours to recharge the implanted battery. The energy should be transmitted wireless to the implanted battery via appropriate antenna. The system can also comprise a cradle for charging the recharge unit. Charging can be performed through a wired or metal contact connection. The battery provides sufficient energy for at least one month operation of the medical device. Recharge time is less than 6 hours. In another preferred embodiment, the source of energy is at least one implantable primary (i.e. non-rechargeable) battery, having advantageously a lifetime of at least 4 years for a volume of 3.7 $cm^3$ (in total 7.4 $cm^3$ if two batteries are used). The battery may be a lithium-manganese dioxide battery.

The battery volume and weight are crucial for implantable devices. Therefore a high power density is needed. Larger batteries with lower power density exist. But if these batteries are too big and heavy, they cannot be implanted. The devices would become too large and e.g. visible under the skin. Further it isn't always possible to accommodate and to fasten the device in the body. Therefore there is a risk of implant movement due to high weight of the device. Heavy devices could be not comfortable for the patient. Moreover, too large and heavy batteries could be justify exclusion of a device for a particular therapy.

The features of the battery depend on the application of the artificial contractile structure, on the pressure to be applied, on the number of contractile elements to activate, and how often the patient opens and closes the contractile structure.

In the present invention, when energy is provided to the electromotor, this energy may be transmitted directly to the lead screw which converts its rotative movement to a lateral movement of the nut or alternatively transmitted directly to the nut to drive it in rotation within the actuator casing so as to move the lead screw laterally with respect to the nut to pull or release the cable. Movements of the nut or the lead screw with respect to each other in the different embodiments of the invention upon transmission of energy from the electromotor triggers advantageously pulling or pushing the cable to close or open the contractile element. No extra release mechanism is required. No or minimal energy is needed to maintain the contractile element in its activated position, which means that the maximum pressure on the organ is maintained with minimal energy consumption. In the case corresponding to minimal energy consumption, only a few electronic components are permanently powered.

Most energy is needed for just a few seconds to drive the nut or lead screw respectively and close or open the contractile element, which also provides significant reduction of the power consumption, that allows a significant increase in the battery life time.

With such lower energy consumption, which was never disclosed in the prior part, the operation time of the battery used as source of energy is comprised between 1 month and 10 years, preferably between 1 year and 10 years, and more preferably between 2 years and 8 years, optimally 5 years, for a battery having a volume of 3 $cm^3$ to 20 $cm^3$.

The medical device of the invention allows therefore the use of a primary battery placed inside the body of the patient, which is to be changed only several years after its implantation, optimally 5 years for a battery having a volume of 3 $cm^3$ to 20 $cm^3$. Therefore the medical device of the invention need no accumulator or rechargeable battery, which is an advantage compared to the devices of the prior art.

Moreover, the motor, the gear ratio and the lead screw have been chosen in such a way that the travel time for the nut or the lead screw between the resting position and the activated position is comprised between 0.2 s and 90 s, for a travel of the nut or the lead screw comprised between 2 mm and 50 mm, preferably between 3 mm and 15 mm. Preferably, the travel time needed by the nut or the lead screw for moving between the resting position and the activated position is comprised between 0.4 s and 60 s, more preferably between 0.5 s and 10 s, and more preferably between 0.5 s and 5 s for a travel of the nut or the lead screw comprised between 2 mm and 50 mm, preferably between 3 mm and 15 mm.

The time for opening or closing the contractile element could be different and depends on the material of the contractile element.

The appropriate electromotor is commercialized for example by Maxon Motor AG, Faulhaber or Portescap. Preferably, the gear ratio is comprised between 4 and 64, and preferably between 16 and 64. The lead screw has a pitch comprised between 1 and 3 and an effective diameter comprised between 2 mm and 4 mm.

The following strategies have been worked out to reach a high efficient and power saving device.

First, the requirements for battery system in implant should be a very high power density, low self discharge rates, low serial impedance for medium pulse power demands, negligible voltage delays, guaranteed rated capacity, and reliable definition of end of life (EOL) condition.

Moreover, the system concept of electronic design shall provide power saving modes (e.g. switch-off unused parts, minimize current consumption of permanent powered parts), consume electrical power directly from battery, minimize serial impedances in the power paths, ensure a reliable detection of battery EOL condition, and minimize current consumption during idle mode.

The system concept of mechanical design shall provide actuator system which ensures high efficiency, low starting voltages and simple control, ensure no permanent current consumption, and provide fast and low power position control.

The system concept of wireless communication design shall meet ultra low-power design challenges and ensure low error rates.

The key points to get a high efficient and power saving medical device of the invention were:
  two implantable primary batteries (non-rechargeable);
    chemistry: Lithium-Manganese Dioxide
  ultra low power consumption (<6 µA) during idle mode;
    only few active parts are permanently powered design provides several power saving modes (stop mode+ several intermitted modes)

wireless communication based on medical implant communication service (MICS)—duty cycle sniffing for wake-up actuator system based on high performance DC motors, combined with gear box and lead screw deliverable as a compact unit gear box with self-retention ensures powerless hold detection of lead nut or lead screw position (travel measurement) with a linear membrane sensor for precise measurements and lowest current consumption.

The medical device of the invention can comprise only one actuator, the transmission means being designed to transmit the forces induced by the actuator to each of the contractile elements of the structure.

In other embodiments, the medical device can comprise several actuators, each actuator being associated, via appropriate transmission means, to one or several contractile elements.

The artificial contractile structure may be a structure comprising separate contractile elements described above or linked by a support.

In some embodiments, the artificial contractile structure may comprise at least two contractile elements, which can be independent or distributed along a support, in order to be able to reduce the volume of the organ to be contracted in at least two distinct regions of said organ. The device may comprise at least two actuators respectively linked to their corresponding contractile element by their corresponding transmitting means.

If the structure comprises several contractile elements, said contractile elements can be designed in such a way that each contractile element is connected to an adjacent contractile element, while remaining flexible one with respect to the other. That means that a contractile element and its adjacent contractile element are physically linked or connected to each other, directly or indirectly, by an appropriate connecting element, allowing one to obtain a compromise between the stiffness and the flexibility of the structure. This structure allows applying to minimal pressure to the tissues avoiding tissue necrosis and damage. Moreover, this structure allows optimal pressure control and implantation of the structure by surgeons, by having a single-piece device, which is adaptive to the natural flexibility of the urethra while remaining semi-rigid so that the structure stays in place and the pressure of each contractile element can be optimally synchronized.

In some embodiments, the artificial contractile structure may further comprise a first flexible connecting element designed to link each contractile element to an adjacent contractile element, said connecting element being made out of elastic biocompatible material for keeping said contractile elements in longitudinal position while allowing a rotational movement of each contractile element one with respect to the other. Such first flexible connecting element may be fastened directly to the connecting elements.

In other embodiments, two adjacent transmissions means are merged in such a way that the two corresponding adjacent contractile elements are indirectly connected In some embodiments, the medical device further comprises at least one second connecting element designed to merge the adjacent transmissions means of two adjacent contractile elements, in such a way that said adjacent contractile elements are indirectly connected via their transmissions means, and more particularly via the cables linking the actuators to the adjacent contractile elements. Such second connecting element may be bars or other similar connecting elements used to merge said two adjacent transmission means. In other embodiments, the transmissions means may be merged by overmolding. In this manner, the contractile elements may be kept in longitudinal position while allowing a rotational movement of each contractile element one with respect to the other.

Advantageously, each contractile element is flexible so that it has the freedom to move longitudinally no more than 5 mm to each direction, preferably no more than 3 mm to each direction, and more preferably no more than 1 mm to each direction from an adjacent contractile element, and so that it can move according to a transversal rotation no more than 30°, to each side, preferably no more than 20° to each side from an adjacent contractile element, allowing the most flexibility and independence of each contractile element from its adjacent contractile elements preventing a peristaltic movement of the whole device along the urethra and allowing optimal synchronization of the contractile elements.

In some embodiments, the control unit may be adapted to pulsatory and alternately activate each contractile element, independently from each other. The actuators are preferably controlled by the same control unit.

In some embodiments, the medical device may further be combined with a device that signals the patient that the contractile structure will open soon, e.g. within next five minutes. This embodiment is preferred if the organ is the bladder, so that the patient has time enough to go to the toilet. The signaling device can be for example a vibration alarm or a LED. The medical device may also further comprise an automated closing feature that the device automatically closes after e.g. 3 min. This has the advantage in case the patient forgets to close.

In the invention, the contractile structure is placed around an organ to be contracted or is placed on (or close to) an organ so that a local pressure is applied to such organ. It may comprise one or more contractile elements disposed around the organ.

A medical device of the invention that has one or more contractile elements placed on an organ (so that a local pressure on such organ is achieved, preferably in a pulsatory manner) may be easier to implant for surgeons, because delicate and/or lengthy surgery around the organ is avoided. In the field of incontinence, this device may however be less convenient for full control of incontinence compared to a device whereby the contractile structure is around the urethra. Such medical device (that has one or more contractile elements on an organ) is however superior to the commercial slings used to control urinary incontinence which have poor success rates (see Retropubic versus Transobturator Midurethral Slings for Stress Incontinence, Holly E. Richter et al. The New England Journal of Medecine, 2010; 362:2066-79). Therefore the contractile structure of the medical device of the invention may be designed as a classical sling in terms of shape and dimensions so that a controlled (by the patient) local pressure is applied on the urethra, therefore maximizing control of incontinence. Hereby such device is defined as an "active sling".

This active sling may not be limited by the embodiments of the present invention, meaning that contractile element may be activated mechanically by hydraulic or pneumatic means as described for in the prior art AMS800 device. Preferably, however a source of energy for powering is used, but the energy consumption of said medical device may be even lower than 50 mAh/year for a pressure applied by the contractile element on the organ comprised between 0.1

N/cm² and 5 N/cm², for a battery having a volume between 3 cm³ and 20 cm³. Interestingly even a small pressure on the urethra that is managed by an active sling will improve control of incontinence compared to traditional slings.

Preferably, this active sling is adapted to be placed, at least partially, in a female or male patient in one of several locations, i.e., below the pubis bone, so as to lift the urethra from a point below the pubis bone when the patient is standing, into the pubis bone, so as to lift the urethra from a point attached to the pubis bone of the patient, or above the pubis bone of the patient, so as to lift the urethra from a point above the pubis bone when the patient is standing.

The urethra is lifted by reducing the length of the u-shaped traditional sling. Normally the device forms a loop and the adjustment changes the length of the loop to lift the urethra. The loop can have any shape or form that can be used to lift the urethra when placed inside the loop, when implanted. The device forms a loop that is placed around stable tissue. The loop holds up the urethra, when placed inside the loop, when implanted. Preferably, the interconnecting part is a band or a thread, or a plurality of bands or threads connected to each other to lift the urethra.

The resting position of the contractile element of the structure corresponds to a state in which any force is transmitted by the transmitting means to the contractile element, and the activated position corresponds to a state in which a force has been transmitted in such a way that the contractile element closes and constricts the organ to be contracted.

In some embodiments, the contractile element is made out of biocompatible materials, preferably selected from the group consisting of silicone and polytetrafluorethylene (PTFE), polylactide (PLA)-polymer, polyurethane (PUR), Polymethylmethacrylate (PMMA), polyoxymethylene (POM), HDPE polyethylene and LDPE polyethylene or combinations thereof. Other appropriate material as other polymers or metal can be used.

The contractile element of the contractile structure may have the form of an open ring to be placed around the organ or around a hollow part of the organ to be contracted, said ring having a moving part linked to the transmitting means.

Preferably, the contractile element comprises a moving part linked to the actuator and designed to move, when activated by the actuator, between the activated position and the resting position of the contractile element.

Advantageously, the contractile element comprises a band which surrounds at least partially the organ to be contracted, and the transmission means are designed to be linked to one end of the band and to pull it, when the contractile element is activated by the actuator, in such a way that said contractile element reaches its activated position.

Preferably, the transmitting means are a cable, and the band may comprise at one end a point for linking the cable and at the other end a hole crossed by said cable.

In some embodiments, the size of the band may be comprised between 4 cm and 15 cm in length, preferably between 4 cm and 12 cm in length, and between 3 mm and 15 mm in width, preferably between 3 mm and 12 mm in width.

The control unit and/or power supply unit includes electronics and software designed to:
control and adjust the actuator generating the force transmitted to the contractile element
provide control of the actuator from outside the body through wireless connection
optionally recharge the internal battery through wireless connection
control the status of the battery
provide test and diagnosis support for health care professionals
handling of alarm conditions and exceptions.

The control unit comprises a microprocessor that distributes current to actuators so that they activate the contractile elements pulsatory, at the required pressure and at the required frequency.

The microprocessor can be adjusted via remote control individually for each patient regarding pressure and frequency of opening and closing.

Ideally, these adjustments can be done after implantation transcutaneously, preferably by a medicinal physician, in order to optimize control of volume reduction (such as incontinence leaking). Readjustments can be performed at any time during the life time of the device using a remote control, as described below.

The number of contractile elements to contract can be adapted to the required pressure to apply on the organ. For example, in the case of urinary sphincter, the number of contractile elements to open and close can be adapted to the abdominal pressure.

The pressure of the structure on the region of the organ to be contracted may be comprised between 0.1 N/cm² and 5 N/cm², and preferably between 0.3 N/cm² and 2.5 N/cm².

In a preferred embodiment, the device of the invention comprises:
i) an artificial contractile structure implantable into the human body and comprising one or more contractile elements able to be activated by an actuator as described above,
ii) at least one implantable actuator which upon activation will induce a contraction of the contractile elements, such as the actuators described above,
wherein the actuator and the contractile elements are designed so that the pressure, applied on the organ to be contracted, is comprised between 0.1 N/cm² and 5 N/cm², and preferably between 0.3 N/cm² and 2.5 N/cm² during a period comprised between 30 seconds and 90 minutes, preferably between 30 seconds and 60 minutes, more preferably between 30 seconds and 45 minutes, and more preferably between 10 minutes and 30 minutes.

Each contractile element is preferably activated or deactivated several times a day, and most preferably several times an hour. The contractile elements may be activated, in a pulsating and alternating manner, a pressure on an organ to be contracted during a period comprised between 30 seconds and 90 minutes, preferably between 30 seconds and 60 minutes, more preferably between 30 seconds and 45 minutes, and more preferably between 10 minutes and 30 minutes. The relaxation time is dependent on the number of regions, which are to be contracted by the independent contractile elements.

If the artificial structure is adapted to contract for example four regions of an organ, and if only one contractile element is activated at the same time, each contractile element can be activated during one minute and deactivated during three minutes in an alternating manner. In another embodiment, each contractile element can be activated during five minutes and deactivated during fifteen minutes in an alternating manner. If the structure is adapted to contract three regions of an organ, each contractile element can be activated during one minute and deactivated during two minutes in an alternating manner. If the structure is adapted to contract two regions of an organ, it comprises two contractile elements, which can be activated during 30 minutes and deactivated during 30 minutes in an alternating manner.

The activation of each contractile element can be random or sequential.

Only one of the contractile elements or several contractile elements can be contracted at the same time. In other embodiments, one contractile element can remain contracted or closed whereas another contractile element is contracted or closed.

Advantageously, the medical device comprises a control unit which is designed so that at least two contractile elements are able to be maintained in the same position at the same time. This feature of the medical device may be used separately or in combination with anyone of the features of the medical device described above.

Preferably, at least two contractile elements are able to be maintained in their activated position at the same time.

If the patient wishes to do sport, several or all the contractile elements may be closed in such a way that the pressure, which is applied on the organ to be contracted, is increased for a certain time, typically 1 h. After that time the system goes back into the alternately activation controlled by the control unit. To avoid tissue damage sports mode can't be activated more than twice in a raw and not more than maximum 3 hours a day.

Advantageously, the control unit is designed so that at least two contractile elements are able to be maintained in their resting position at the same time.

During the night, several or all the contractile elements may be maintained in a resting position, without any contraction in such a way that the energy consumption is reduced.

All these embodiments are obtained by means of an adequate control unit. Said control unit is designed to allow an adjustment of the pressure of the contractile structure on the organ according to the patient's need, by adjusting the force generated by the actuator and the frequency the contractile structures are acting. Advantage is that the physician can customize the optimal pressure of the contractile structure to side effects on the organs, for example by means of a magnet placed around the device. The parameters of the control unit and also of the actuator can be adjusted by the physician after the implantation of the device during the postoperative consultations.

The control of the contractile structure and more especially its opening can be achieved, by the physician or the patient himself, by a manual control of the control unit by means of a remote control to open and close the urethra. The remote control is preferably wireless. For the physician, the remote control can be designed to enable adjustments of the medical device (activation force, parameters of the pulsatory and alternately activation, test and diagnosis mode). An optical signal and/or vibration signal may be provided in order to show the patient the level of the battery status. Two different remote controls can be provided: a simple remote control for the patient and an advanced remote control for the healthcare professionals. The patient gets a simple remote control to open and close the contractile structure and to get few information like battery status and device status. The healthcare professionals have an advanced remote control that in addition allows to readjust the pressure and frequency, move the device into the examination mode as described below (motor will move typically 5 mm in the opposite direction of closing the contractile structure) reading implant parameters.

For emergency, the control unit may be controlled by means of a switch placed under the skin, which is activated by pressure on one or several buttons. Preferably, the switch comprises several buttons and the sequence for pressing the buttons is predetermined in order to avoid accidental opening of the structure.

Another alternative for safety is the automatic opening of the contractile elements after reaching a certain force (typically 5 N) or pressure.

In other embodiments, the control of the contractile structure and more especially its opening can be achieved, by the physician or the patient himself, by a manual control of the contractile elements themselves by means of a releasing device designed to manually open the contractile structure. Such releasing device can be used if the patient lost the remote control or if a surgeon wishes to open the structure to endoscopically examine the patient or if a kidney stone has to be removed. This corresponds to the examination mode (motor will move typically 5 mm in the opposite direction of closing the contractile structure to totally open the contractile structure) allowing the examination with an endoscope without risk of damage of the urethra.

Advantageously, the closed structure of the invention has a diameter comprised between 8 mm and 35 mm. The dimensions of the open structure are such that, when the contractile element(s) of the structure is/are fully open, the surgeon can move an endoscope through the lumen of the urethra/rectum in order to endoscopically examine the patient. In the same way, the dimensions of the open structure are such that, when the contractile elements of the structure are fully open, kidney stone removal is possible.

Preferably, each contractile element is separated from an adjacent contractile element no less than 1 mm to 2 cm, preferably 2 mm to 1 cm, more preferably 2 mm to 8 mm, for avoiding over-compression.

Preferably, the structure of the invention may be comprise between 2 and 8 contractile elements, so that it makes an overall length comprised between 20 mm and 50 mm.

Examples

Figure 2:
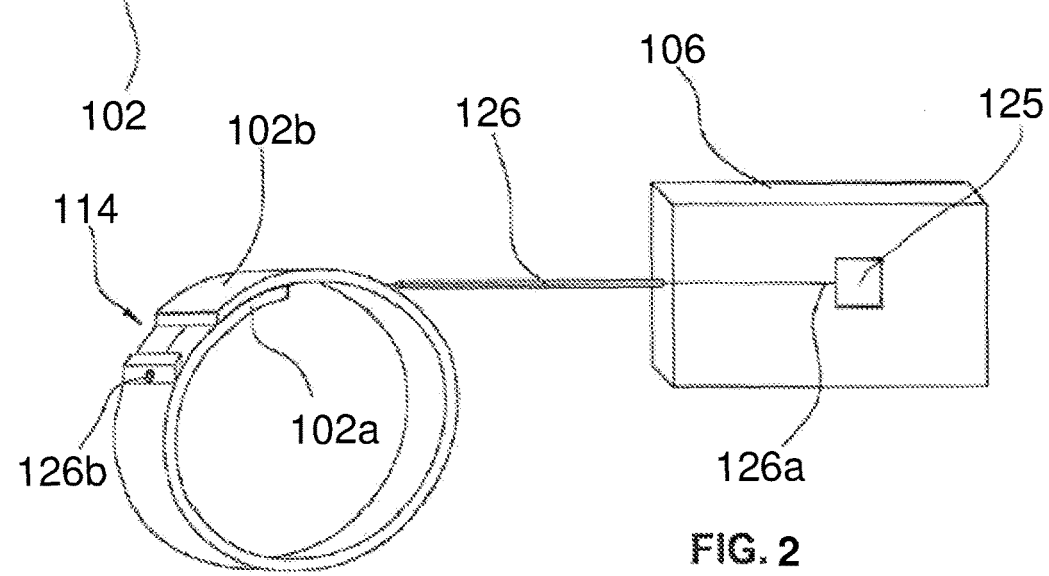
FIG. 2 is a schematic view of the device of FIG. 1, the contractile element being in activated position.

Referring to FIGS. 1 and 2, one embodiment of the medical device of the invention, used to treat urinary incontinence, comprises a contractile element 100 designed to surround partially a hollow part of the urethra, for example. For simplification of the drawings, only one contractile element 100 is shown. But the medical device of the invention may comprise a contractile structure comprising at least two contractile elements 100 adapted to be placed around the hollow part of the urethra, for example, and linked by connecting elements.

The contractile element 100 comprises a band 102 designed to surround at least one time the hollow part of the organ to be contracted. The band 102 is made of silicone, PTFE, PLA, PUR, PMMA, (PQM), HDPE LDPE or combination thereof to reduce the friction when the band wraps closely around the organ. Other appropriate material, such as metal, can be used.

The medical device comprises also an actuator placed in a box 106 away from the organ to be contracted. Such an actuator is linked to the contractile element 100 by a cable 126.

Figure 3:
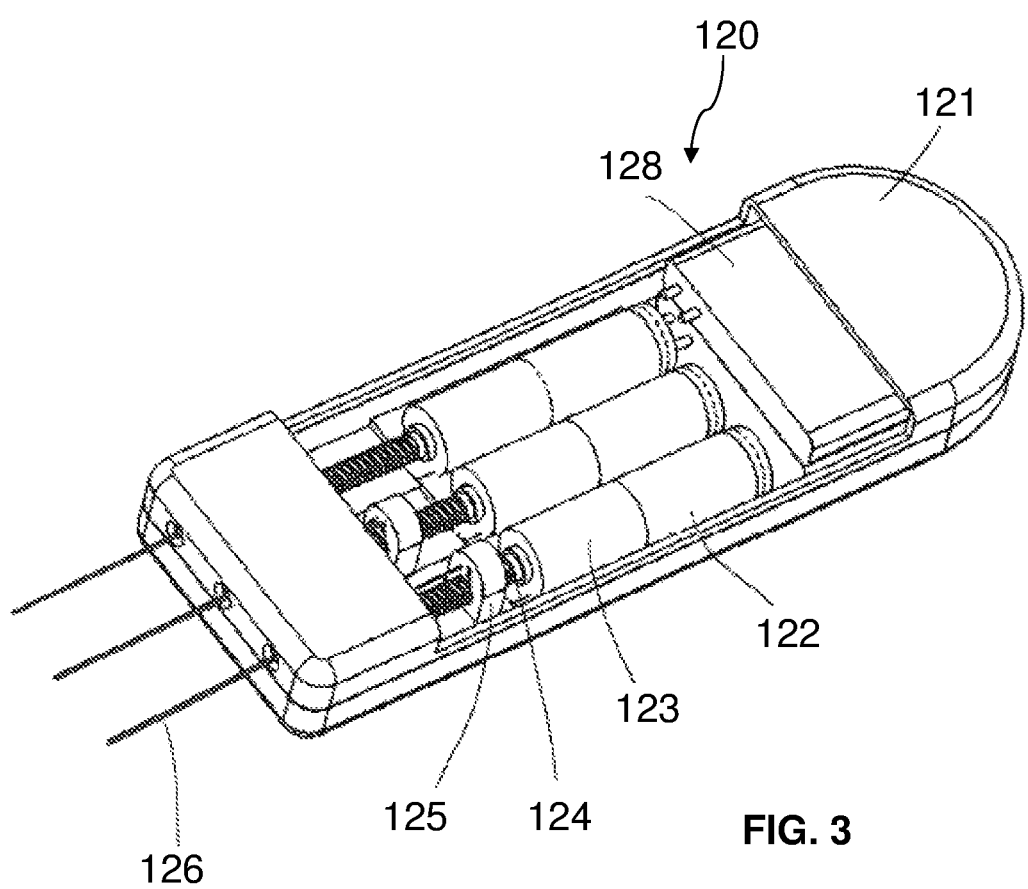
FIG. 3 is a schematic view of a control unit used in the invention.

FIG. 3 shows a control unit 120 used to control and activate the contractile element 100 shown in FIGS. 1 and 2. The control unit 120 is placed in a box 121 made of polymer or titanium. The control unit 120 comprises three actuators, each having an electromotor comprising an electric motor 122, a gearhead 123 connected to said motor 122, a lead screw 124 cooperating with said gearhead 123, and a nut 125 mounted on said lead screw 124. The nut 125 is connected to the cable 126 that transmits the force to the corresponding contractile element 100 to close or open it. The cable 126 is made of stainless steel, titanium or polymer and surrounded by a coaxial sheath 110 of silicon. One end 126a of the cable 126 is connected liquid tight and may be reversibly linked to the nut 125. The other end 126b of the cable 126 is linked liquid tight and may be reversibly linked to one end 102a of the band 102. The other end 102b of the band 102 comprises a hole 112 through which the cable 126 runs.

Soft foam could be placed in the space 114 between the band 102 and the cable 126 to avoid tissue in-growth between the cable 126 and the contractile element 100. Alternatively, the sliding surfaces of the band could be modified to prevent tissue in-growth, for example by coating.

Each nut 125 moves along the corresponding lead screw 124 to close or open the corresponding contractile element 100.

The control unit 120 comprises also a printed circuit board to control the actuators and batteries 128, for example rechargeable batteries. A percutaneous energy transfer supply can be developed for battery recharge.

Figure 5:
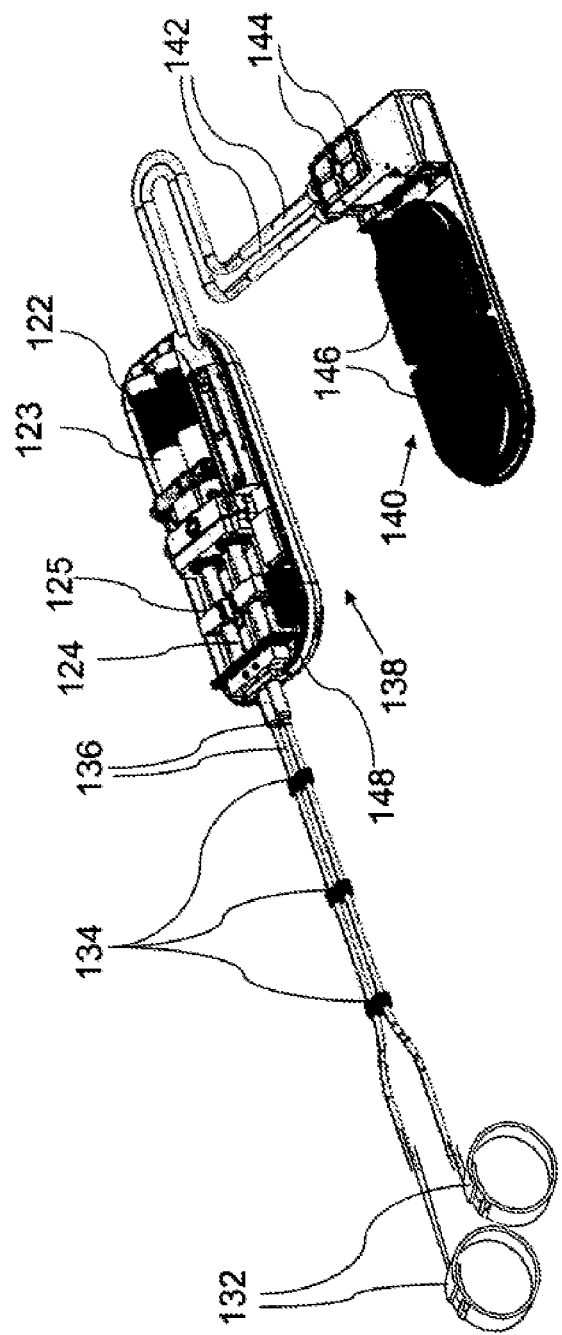
FIG. 5 represents a schematic view of another embodiment of the device according to the invention.

In another embodiment as shown by FIG. 5, two adjacent contractile elements 132 are indirectly connected by using bars 134, said bars being connecting elements fixed around the transmission means and used to merge said two adjacent transmission means, i.e. the two adjacent cables 136.

In this embodiment, the control unit 138 comprises two actuators, each having an electromotor comprising an electric motor 122, a gearhead 123 connected to said motor 122, a lead screw 124 cooperating with said gearhead 123, and a nut 125 mounted on said lead screw 124. The nut 125 is connected to each cable 136 that transmits the force to the corresponding contractile element 132 to close or open it. Each nut 125 moves along the corresponding lead screw 124 to close or open the corresponding contractile element 132.

The control unit 138 is separated from the energy source. The energy source is in the power supply unit 140 that is connected to the control unit 138 by electric cables 142, which are easily detachable by using connectors 144. The energy source comprises two implantable primary 146 (i.e. non-rechargeable) batteries, each having a lifetime of at least 4 years for a volume of 3.7 cm$^3$.

FIG. 6 represents a further alternative of a control unit 150 a control unit used to control and activate a contractile element 100 as shown in FIGS. 1 and 2. The control unit 150 is placed in a casing 151 made of biocompatible material, such as a polymer or titanium. The control unit 150 comprises in this example, as opposed to the control unit 120 of FIG. 3, only one actuator comprising an electromotor including an electric motor 152 and a gearhead 153 connected to said motor 152. The actuator further comprises a lead screw 154 connected at a first end to a transmission cable 156 that transmits the force to a corresponding contractile element, not represented on the figure, to close or open it in operation. In that embodiment the gearhead 153, engages directly and cooperates in rotation with a nut 155 fixedly mounted in the casing along a longitudinal axis thereof, coincident with the longitudinal axis of the lead screw 154, but free in rotation about said longitudinal axis and under the driving force of the gearhead 153 thanks to two bearings 156. The lead screw 154 is connected to the cable 156 and is movable along said longitudinal axis upon rotation of the nut 155, with which it cooperates under a helicoidal link.

The cable 156 may be made of stainless steel, titanium or polymer and surrounded by a coaxial sheath, for example of silicon. The cable 156 is connected liquid tight and may be reversibly linked to the lead screw 154. The other end of the cable 156 is linked liquid tight and may be reversibly linked to the band 102 of a contractile element.

The control unit 150 may comprise also a printed circuit board to control the actuator operated by batteries, not represented in the figure.

A travel sensor is provided in such a way that the control unit 120 or 138 knows the exact position of the nuts 125 and therefore the position of each contractile element 100 or 132. It is also needed for the readjustment of the force.

In case of power loss the control unit comprises a capacitor 148 which has enough energy stored to apply to the electromotors and to open the contractile elements 100.

In FIG. 1, the contractile element 100 has not been contracted. The nut 125 is closer to the contractile element 100, which is in a resting position, the band 102 being loosely wrapped around the organ.

When an electric current is applied to an electromotor by the control unit 120 or 138, the corresponding lead screw 124 rotates in such a way that the corresponding nut 125 is moving along the corresponding lead screw 124. If the nut 125 moves away from the contractile element 100 or 132, the nut 125 pulls on the corresponding cable 126, which pulls on the corresponding contractile element 100 or 132 to close it. More especially, the nut 125, by moving away from the contractile element 100 or 132, moves the end 126a of the cable 126 into the box 121. So that the other end 126b of the cable 126 is moved as the same way. By moving, the end 126b of the cable 126 pulls on the end 102a of the band 102, which slides under the other end 102b, until the band 102 is closely wrapped around the organ to constrict it. The contractile element 100 or 132 is then in an activated position as shown by FIG. 2 or FIG. 5.

Almost no energy is needed to maintain the contractile element 100 or 132 in its activated position. Only a few electronic components are permanently powered.

When the contractile element 100 or 132 has to come back in its resting position, the control unit 120 or 138 supplies electrical energy to the electromotor, in such a way that the lead screw 124 rotates in the opposite direction. The nut 125 comes closer to the contractile element 100 or 132. Then, the cable 126 is not pulled by the nut 125 any more in such a way that the contractile element 100 or 132 comes back to its resting position as shown by FIG. 1.

If several contractile elements 132 are used to form a contractile structure and constrict the organ in distinct regions, as shown by FIG. 5, each contractile element is linked to its actuator by the corresponding transmitting means. The control unit is therefore adapted to distribute current to each actuator, preferably in order to pulsatory and alternately contract the contractile elements 100.

In this case, there are several gates, which can be independently, pulsatory and alternately activated in order to contract one or the other region around which the contractile elements 100 or 132 have been placed, in a pulsating and alternating manner. This allows an alternate contraction along the urethra, several times an hour. Such a configuration avoids stressing of the underlying tissue followed by erosion and necrosis.

The control unit is designed to activate at least one actuator and therefore to activate at least one contractile element so that at least one region of the urethra is closed to avoid incontinence. The patient deactivates the device if necessary, so that each actuator is inactivated to open each region of the hollow part of the urethra, allowing the passage of the urine.

There are also means for opening on demand said artificial contractile structure, used by the physician or the patient himself to inactivate the actuators and open the contractile elements.

The device can further comprise sensing means selected from pressure, and force sensing means.

Obviously, the device of the invention can be used with a control unit adapted to drive the contraction of the contractile elements, on demand, without pulsatory and alternately contracting said contractile elements.

The operating time of the medical device as shown by FIG. 5 was tested for different travels of the nut 125 and for different cycle times. The travel is the distance covered by the nut 125 moving along the lead screw 124 in such a way that the contractile element 132 moves between its resting and activated positions. A cycle time comprises movement of the nut for closing the contractile element, time for which the contractile element is closed, movement of the nut for opening the contractile element and time for which the contractile element is opened.

The travels were 10 mm, 8 mm and 5 mm. The cycle times were 10 minutes, 20 minutes and 30 minutes.

The electromotor comprised the motor 08GS61 from Portescap, lead screw pitch is 1.80 mm and the diameter is 2.00 mm; gear ratio is 16.

The control unit comprises as source of energy two primary batteries of 1.1 Ah, with an assumed shelf life of 1 year, for a volume of 3.7 cm$^3$ each.

The pressure applied by the contractile element on the organ was 1.5 N.

Figure 4:
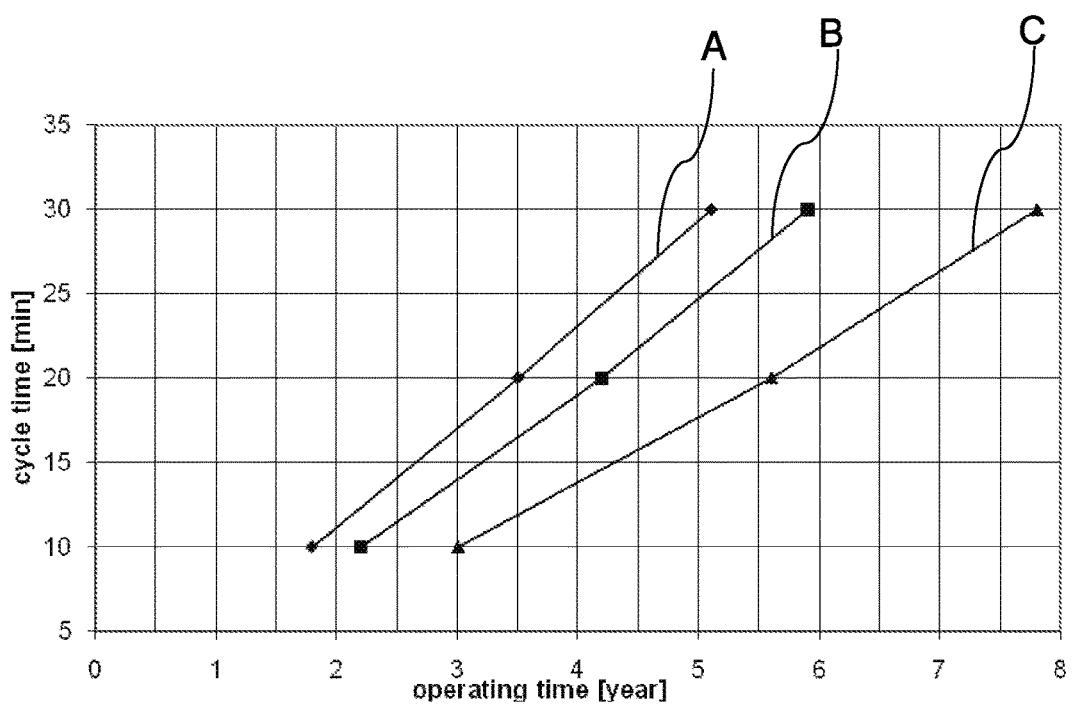
FIG. 4 represents the cycle time as a function of the operating time for a device of the invention using primary batteries.

The results are shown by FIG. 4, which represents the cycle time as a function of the operating time for different travels for a travel of the nut of 10 mm (curve A), a travel of 8 mm (curve B) and a travel of 5 mm (curve C). FIG. 4 shows that the medical device of the invention allows to use primary batteries enabling to obtain an operating time of 1.8 years to 7.8 years.

This medical device comprising primary batteries was compared with a similar medical device but using a rechargeable battery of 200 mAh.

The travel of the nut was 10 mm and the pressure applied by the contractile element on the organ was 1.5 N.

In the first case, the cycle time was 10 minutes and in the second case, the cycle time was 30 minutes.

The results are shown in the Table below:

| Type of power supply | Volume power supply | Typical operating time before exchange/recharge | |
|---|---|---|---|
| | | cycle time = 10 min. | cycle time = 30 min. |
| Rechargeable Battery 200 mAh | 3.3 ml + TET | 2 months | 5.5 months |
| Primary Battery 2 × 1.1 Ah | 7.4 ml | 1.8 years + 1 year shelf life | >5 years + 1 year shelf life |

The Table shows that the medical device of the invention using an electromotor and a primary battery has an operating time of more than 5 years before exchange of the battery, with a cycle time of 30 minutes, and of 2 years with a cycle time of 10 minutes.

Moreover, such a medical device allows applying minimal pressure to the tissues thereby avoiding tissue necrosis and damage, even if each contractile element applies a pressure at a frequency of 30 to 45 minutes alternately with the other contractile elements. That means that every contractile element is closed for 30 to 45 minutes alternately with the other contractile elements. A device as AMS 800 shows erosion because the device is closed for about 6 to 8 hours per night and during the day for about 4 hours, assuming that the patient goes every 4 h to the toilet.

The invention claimed is:

1. A medical device comprising:
   an artificial contractile structure comprising at least one contractile element adapted to contract an organ, said contractile element being in a resting position or in an activated position, the activated position being defined by said contractile element constricting the organ and the resting position being defined by said contractile element not constricting the organ,
   at least one actuator designed to activate said contractile structure, and
   at least one source of energy for powering said actuator,
   wherein the actuator comprises an electromotor and a transmission element linking the electromotor to the contractile element, the transmission element comprising a cable and being configured to transmit to the contractile element a force induced by the electromotor, and
   wherein said electromotor comprises an electric motor, a gear head connected to said motor, a lead screw cooperating with a nut mounted on said lead screw, said lead screw or said nut being connected to said transmission element and cooperating with said gear head to transmit said force induced by the electromotor on said transmission element, and
   wherein the ratio of current needed to maintain the contractile element in the activated position/current needed to change the position of the contractile element is less than 1/500.

2. The medical device according to claim 1, wherein the ratio of current needed to maintain the contractile element in the activated position/current needed to change the position of the contractile element is between 1/20000 and 1/500.

3. The medical device according to claim 1, wherein the energy consumption of said medical device is less than 2000 mAh/year.

4. The medical device according to claim 1, wherein the energy consumption of the medical device is less than 1800 mAh/year.

5. The medical device according to claim 1, wherein said at least one source of energy has a volume less of than 20 cm3.

6. The medical device according to claim 1, wherein the at least one source of energy has an operation time of between 2 months and 10 years.

7. The medical device according to claim 1, wherein the transmission element comprises a cable linking the nut or the lead screw to the contractile element.

8. The medical device according to claim 1, wherein the actuator further comprises sensors designed to indicate the position of the nut or the lead screw.

9. The medical device according to claim 1, wherein the contractile element comprises a moving part linked to the actuator and designed to move, when activated by the actuator, between the activated position and the resting position of the contractile element.

10. The medical device according to claim 1, wherein the contractile element comprises a band which surrounds at least partially the organ to be contracted, and wherein the transmission element is configured to be linked to one end of the band and to pull it, when the contractile element is activated by the actuator, in such a way that said contractile element reaches its activated position.

11. The medical device according to claim 1, wherein the source of energy comprises at least one implantable rechargeable battery with an implantable antenna and an external battery.

12. The medical device according to claim 1, wherein the source of energy is at least one implantable primary battery.

13. The medical device according to claim 1, wherein the artificial contractile structure comprises at least two contractile elements configured to reduce the volume of the organ to be contracted in at least two distinct regions of the organ.

14. The medical device according to claim 13, further comprising at least two actuators respectively linked to their corresponding contractile element by their corresponding transmission element.

15. The medical device according to claim 13, wherein each contractile element is connected to an adjacent contractile element, while remaining flexible with respect to the other.

16. The medical device according to claim 15, wherein the artificial contractile structure further comprises a first flexible connecting element configured to link each contractile element to an adjacent contractile element, said first connecting element being made out of elastic biocompatible material and is configured to keep said contractile elements in longitudinal position while allowing a rotational movement of each contractile element one with respect to the other.

17. The medical device according to claim 13, wherein two adjacent transmission elements are merged in such a way that the two corresponding adjacent contractile elements are indirectly connected.

18. The medical device according to claim 17, further comprising at least one second connecting element configured to merge the adjacent transmission elements of two adjacent contractile elements.

19. The medical device according to claim 13, further comprising a control unit which is adapted to activate each contractile element pulsatory and alternately independently from each other.

20. The medical device according to claim 19, wherein the control unit is configured so that at least two contractile elements are able to be maintained in their activated position at the same time.

21. The medical device according to claim 19, wherein the control unit is configured so that at least two contractile elements are able to be maintained in their resting position at the same time.

22. The medical device according to claim 1, wherein the actuator is configured so that the contractile element applies a pressure on an organ to be contracted for a period of between 30 seconds and 90 minutes.

23. The medical device according to claim 1, wherein the actuator is separated from the contractile structure.

24. The medical device according to claim 1, wherein said lead screw is connected to said transmission element.

25. The medical device according to claim 1, wherein said nut is connected to said transmission element.

* * * * *